United States Patent [19]

Siliprandi et al.

[11] Patent Number: 4,780,308

[45] Date of Patent: Oct. 25, 1988

[54] USE OF L-CARNITINE IN THE TREATMENT OF TOXIC EFFECTS INDUCED BY THE INHALATION OF HALOTANE AND OTHER HALOGEN-CONTAINING GENERAL ANESTHETICS

[75] Inventors: Noris Siliprandi; Guido Scutari, both of Padova, Italy

[73] Assignee: Sigma-Tau Industrie Farmaceutiche Riunite S.p.A., Rome, Italy

[21] Appl. No.: 69,256

[22] Filed: Jul. 2, 1987

[30] Foreign Application Priority Data

Jul. 4, 1986 [IT] Italy ............................... 48228 A/86

[51] Int. Cl.$^4$ ........................................... A61K 31/225
[52] U.S. Cl. ...................................... 424/10; 514/547
[58] Field of Search .................. 424/10; 514/547, 922

[56] References Cited
PUBLICATIONS

Toninello et al. "L-carnitine effect on Halothane-Treated Mitochondria," Biochem. Pharmacol., 35(22), pp. 3961–3964, 1986.

Branca et al., "Involvement of Long-chain Acyl CoA in the Antagonist Effects of Halothane and L-carnitine on Mitochondrial Energy Linked Processes," Biochem. Biophys. Res. Commun., 139(1), 303–307, 1986.

Primary Examiner—Stanley J. Friedman
Assistant Examiner—R. Kearse
Attorney, Agent, or Firm—Bruce M. Collins

[57] ABSTRACT

Oral or parenteral administration of 10 to 30 mg/kg/day of L-carnitine (or an equivalent amount of a pharmacologically acceptable salt thereof) both during preanesthesia and post-operative phase antagonizes the toxic effects (particularly on kidneys and liver) induced by inhalation of halogen-containing general anesthetics such as, typically, halotane.

1 Claim, 3 Drawing Sheets

USE OF L-CARNITINE IN THE TREATMENT OF TOXIC EFFECTS INDUCED BY THE INHALATION OF HALOTANE AND OTHER HALOGEN-CONTAINING GENERAL ANESTHETICS

The present invention relates to a novel therapeutical use of L-carnitine. According to its broadest aspect, this novel use relates to the antagonizing treatment of the toxic effects induced by the inhalation of halogen-containing general anesthetics such as, typically, halotane (2-bromo-2--chloro-1,1,1-trifluoroethane) and, furthermore, methoxyflurane (2,2-dichloro-1,1-difluoroethyl methyl ether), enflurane (2-chloro-1,1,2-trifluoroethyl difluoromethyl ether) and isoflurane (1-chloro-2,2,2-trifluoroethyl difluoromethyl ether). Both for simplicity's sake and because halotane is the most widely used inhalational anesthetic, reference will be made hereinbelow to this anesthetic only. It should be understood, however, that whatever is described equally applies to the other above-mentioned inhalational anesthetics.

Halotane is a potent anesthetic which induces a rapid and smooth loss of consciousness and warrants a profound and lasting abolition of responses to painful stimulation. Its vast clinical popularity is based primarily on the ease with which depth of anesthesia can be changed, the rapid awakening when its administration is discontinued and the relatively low incidence of toxic effects associated with its use.

These toxic effects, however, are particularly serious because halotane exerts a depressing activity on the cardiovascular system and induces a profound hypotension. Also cardiac arrhythmias and respiratory insufficiency may result.

The existence of halotane-induced hepatitis has eventually been accepted by the vast majority of hepatologists. Moreover, a higher incidence was detected when patients were administered halotane on two or more occasions over a limited time period.

Furthermore, some cases of malignant hyperpyrexia have been reported.

With regard to toxic effects to the kidneys, urinary oxalate crystals have been detected.

At cerebral level, recovery of mental function after even brief anesthesia with halotane is not complete for several hours.

It has now been found that these toxic effects can be prevented or antagonized effectively by orally or parenterally administering L-carnitine both during pre-anesthesia and immediately following surgery.

Previous therapeutical uses of L-carnitine are already known. For instance, L-carnitine has been used in the cardiovascular field in the treatment of acute and chronic myocardial ischaemia, angina pectoris, cardial arrhythmias and insufficiency. In nephrology, L-carnitine has been administered to chronic uraemic patients who are subjected to regular haemodialysis treatment with a view to counteracting muscular asthenia and the onset of muscular cramps. Further therapeutical uses are the restoration of the HDL/LDL+VLDL ratio to normal and in total parenteral nutrition.

There is no relationship at all, however, between the previously mentioned, known therapeutical uses of L-carnitine and the novel use which is the subject matter of the present invention.

It is, therefore, unexpected and surprising that, by orally or parenterally administering L-carnitine to patients subjected to anesthesia via the foregoing halogen-containing inhalational anesthetics, it is possible to prevent or antagonize the toxic effects thereof.

Although the daily does to the administered depends on the age, weight and general condition of the elderly subject, utilizing sound professional judgement, it has been found that, generally, from about 10 to about 30 mg of L-carnitine/kg of body weight/day or an equivalent amount of a pharmacologically acceptable salt thereof, is a suitable dose.

L-carnitine is compounded into the pharmaceutical compositions by using the usual excipients, diluents and adjuvant agents which are well-known in pharmaceutical technology for preparing orally and parenterally administrable compositions.

It has also been found that a pharmaceutical composition in unit dosage form which is particularly suited for the foregoing therapeutical uses comprises from about 500 to about 1,000 mg of L-carnitine.

The pharmacological tests which will be hereinbelow described provide the effectiveness of L-carnitine in antagonizing halotane toxical effects.

The pharmacological tests are illustrated with reference to the diagrams of FIGS. 1 to 3 wherein:

FIG. 1 illustrates oxygen composition (traces) and the respiratory control ratios of rat liver mitochondria in the presence and in the absence of halotane and L-carnitine; 1 mg mitochondrial proteins/ml (RLM), 150 $\mu$M ADP or 1.6 $\mu$M carbonylcyanide-m-chlorophenylhydrazone (CCCP) were added when indicated by the arrows; where indicated, 1mM L-carnitine and/or 3 mM halotane were present in the incubation medium. The respiratory control ratios are the average of 10 experimental values ± standard deviation;

Male Wistar albino rats which had been kept fasting for 24 hours were sacrificed by decapitation and their livers immediately immersed in ice-cold 0.25 M sucrose solution and 5 mM N-2-hydroxy-ethylpyperazine-N'-2-ethansulfonic acid sodium salt (Na-Hepes) (pH 7.4). The liver was minced, thoroughly washed and then homogenized in 50 ml 0.25 M sucrose solution, 5 mM Na-Hepes (pH 7.4) using a Potter homogenizer with Teflon pestle. Mitochondria were then isolated by differential centrifugation in the same buffered solution. The protein content of mitochondrial suspensions was assayed according to the Gornall et al. method (J. Biol. Chem. 177, 751 (1949)) using bovine serum albumin as standard.

Mitochondria isolated from rat livers were tested for oxygen consumption at 20° C. with a Clark electrode in 2 ml of an incubation mixture containing 2 mg of mitochondrial proteins. The medium composition was: 100 mM sucrose, 50 mM KCl, 10 mM KH2 PO4, 2 mM MgSO4, 1 mM EDTA, 15 mM Tris-HCl (pH 7.4), 5 mM Na-succinate and 1.25 μM rotenone. Appropriate blanks were run to avoid the possibility of halothane inferences with the electrode in the experimental conditions indicated.

Mitochondrial ATP-ase activity was assayed according to the Baginski et al. method (Methods of enzymatic analysis, H.U. Bergmeyer and K. Gawehn, Eds. vol. 2, p. 876, Academic Press, N.Y. 1979) in the following medium: 200 mM sucrose, 10 mM K-Hepes (pH 7.4), 2 mM MgC12, 5 mM succinate, 1.25 μM rotenone, 1 mM ATP. Mitochondria were incubated at 20° C. for 12 minutes at a concentration of 1 mg of mitochondrial proteins/ml of the incubation mixture. Samples of 300 μl were then collected, deproteinized with 10% trichloroacetic acid and assayed for inorganic phosphate.

The mitochondrial transmembrane potential was measured by monitoring the tetraphenylphosphonium distribution across the mitochondrial membrane with a tetraphenylphosphonium--selective electrode prepared according to the Kamo et al. method (J. Membr. Biol. 49, 105 (1979)) using a calomel electrode (Radiometer K401) as reference electrode. The incubations were carried out at 20° C. with 1 mg of mitochondrial proteins/ml suspension in the same incubation mixture used to monitor the oxygen consumption. The electrode potential was linear to the logarithm of tetraphenylphosphonium concentration with a slope of 59 mV, in agreement with Nernst equation. All the calibration tests were repeated in the presence of halothane in order to exclude any direct interference of the anesthetic with the electrodes.

Halothane was diluted with ethanol to 1 M and added to the incubation mixture immediately before beginning the experiment.

The experiment results are summarized in the figures.

Figure 1:
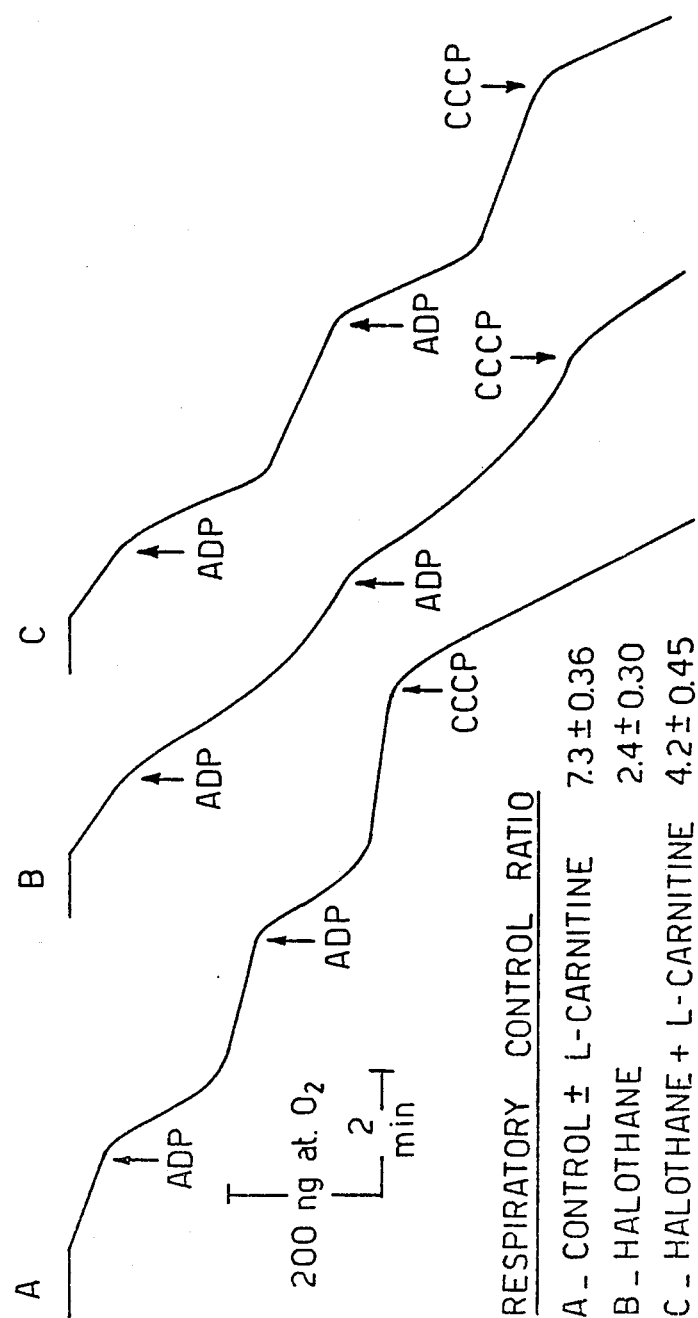

The oxygen traces reported in FIG. 1 indicate that 3 mM halothane significantly decreased the respiratory control ratio of rat liver mitochondria and addition of 1 mM L-carnitine to the medium appreciably improved the respiratory control ratio of halothane-treated mitochondria. L-carnitine did not affect either the respiration rate or the respiratory control ratio of untreated mitochondria. Different compounds structurally or metabolically related to L-carnitine (deoxycarnitine, choline, succinylcholine) proved ineffective in reversing the reported effect of halothane in mitochondrial respiration.

Figure 2:
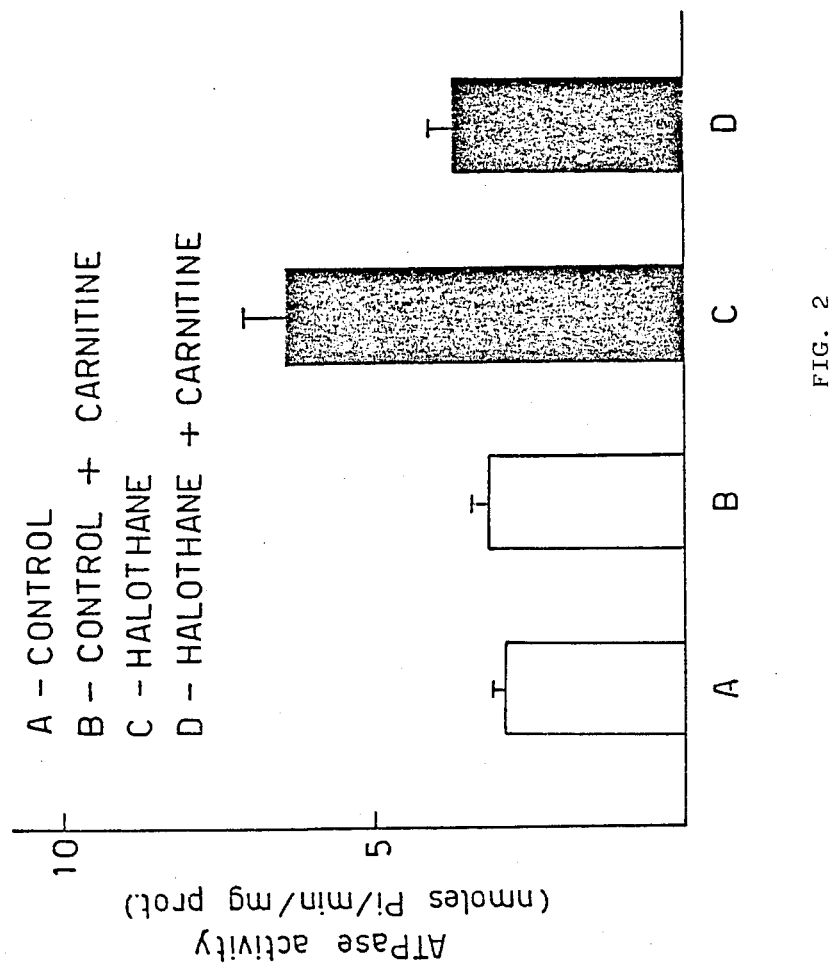
FIG. 2 illustrates the ATP-ase activity of rat liver mitochondria in succinate oxidation in the presence and in the absence of halotane and L-carnitine; where indicated, 1 mM L-carnitine and/or 3 mM halotane were present in the incubation medium. The reported values are the average of 8 different sets of experiments; standard deviations are represented by the vertical bars.

The effects of halothane and L-carnitine on the ATPase activity of mitochondria in oxidizing succinate are reported in FIG. 2. In respiring mitochondria ATP hydrolysis and synthesis are concurrent processes and the resulting release of phosphate is much lower than that obtainable in the absence of any oxidizable substrate. This accounts for the relatively low ATP-ase activity found in such experiments. In these conditions 3 mM halothane caused a two-fold increase of the net ATP-ase activity and 1 mM L-carnitine almost completely reversed this effect.

Figure 3:
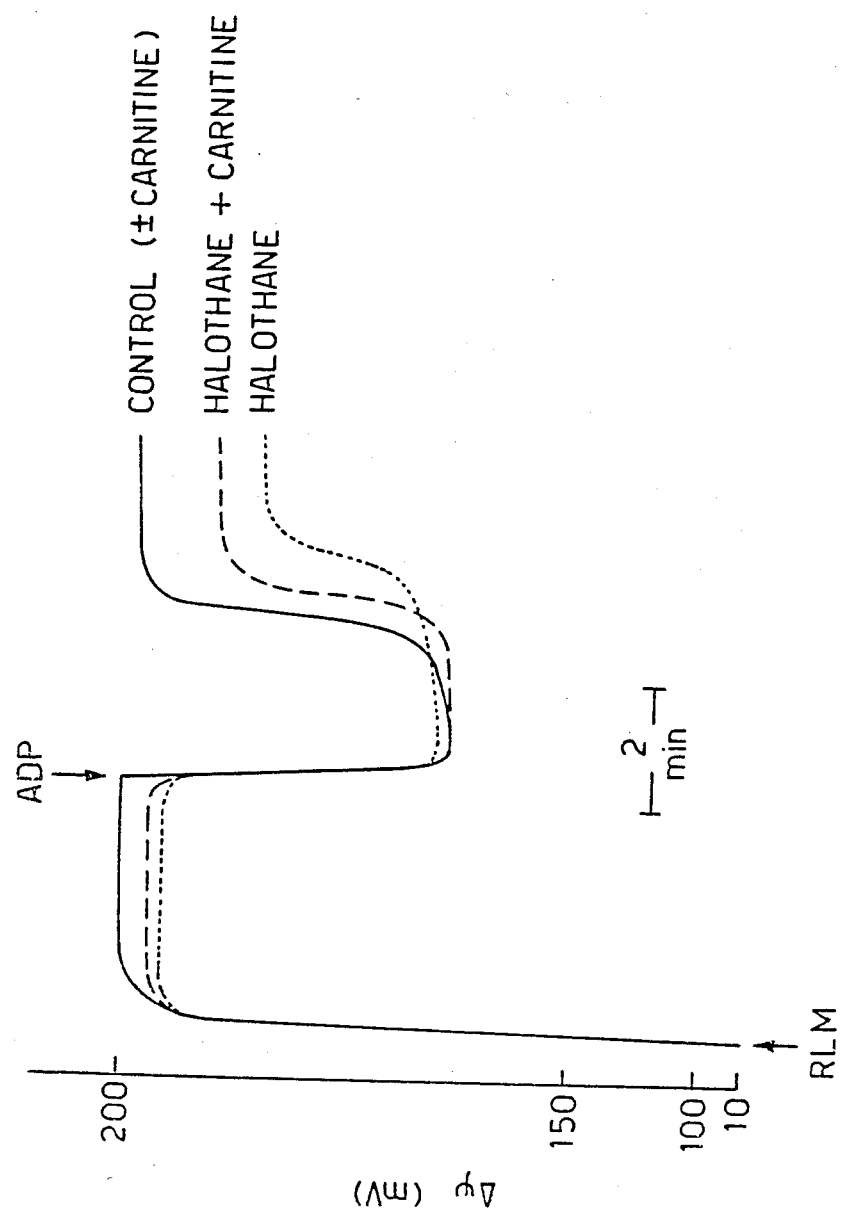
FIG. 3 illustrates the transmembrane potential of mitochondria in the presence and in the absence of L-carnitine and/or halotane; where indicated, 1mM L-carnitine and/or 3mM halotone were present in the incubation medium. 1 mg mitochondrial proteins/mg (RLM) and 150 $\mu$M ADP were added when indicated by the arrows.

The effects of halothane and L-carnitine were also evident on mitochondrial transmembrane potential (FIG. 3). Although halothane did not dramatically modify the transmembrane potential ($\Delta\psi$) attained by rat lever mitochondria during succinate oxidation in state 3, the restoration of $\Delta\psi$ following ADP addition was both decreased and prolonged in the presence of halothane. L-carnitine partially but significantly prevented this effect. The lower steady state of transmembrane potential resulting from ADP additions is caused by the phosphorylation process. The time lenght of this lower steady state is in fact related to the amount of added ADP and $\Delta\psi$ restoration to the original values is dependent on the coupling conditions of the system. Indeed the curves in FIG. 3 indicate that halothane has an uncoupling action which is partially prevented by L-carnitine.

The reported results show that 3 mM halothane (lower concentrations are without effect) added to liver mitochondria alters the properties of mitochondrial membranes, with a consequent decrease of the phosphorylation efficiency. This evidence derives from the results relative to the respiratory control ratio (FIG. 1) as well as to $\Delta\psi$ determination (FIG. 3). The achievement of the same results with different methodologies rules out possible interference of halothane with both the oxygen and tetraphenylphosphonium electrode. Furthermore the stimulation of the ATP-ase activity induced by halothane further confirms that oxidative phosphorylation is partially uncoupled. The problem whether the uncoupling action of halothane might result either from an aspecific perturbation of the mitochondrial membrane or from an interaction with specific sites of the membrane is irrelevant from a patent standpoint.

What is claimed is:

1. The method of preventing and antagonizing the toxic effects produced by a halogen-containing inhalation general anesthetic in a patient submitted to anesthesia which comprises orally or parenterally administering thereto during pre-anesthesia and immediately following surgery in a single or multiple dose regimen from about 10 mg/kg of body weight to about 30 mg/kg of body weight per day of L-carnitine or a therapeutically equivalent amount of a pharmacologically acceptable salt thereof.

* * * * *